United States Patent [19]

Chao

[11] Patent Number: 5,919,445
[45] Date of Patent: Jul. 6, 1999

[54] USE OF GREEN FLUORESCENT PROTEIN TO TRACE THE INFECTION OF BACULOVIRUS IN INSECTS AND TO INCREASE VIRAL UV STABILITY

[75] Inventor: Yu-Chan Chao, Taipei, Taiwan

[73] Assignee: Council of Agriculture Executive Yuan, Taiwan

[21] Appl. No.: 08/877,564

[22] Filed: Jun. 17, 1997

[30] Foreign Application Priority Data

Oct. 9, 1996 [TW] Taiwan .................................. 85112384

[51] Int. Cl.$^6$ ............................ A01N 63/00; C12N 15/00
[52] U.S. Cl. ........................ 424/93.2; 424/93.6; 435/471; 47/58.1
[58] Field of Search .............................. 435/172.3, 235.1, 435/5, 8, 29, 32, 34, 471; 424/93.2, 9.6, 93.6; 47/58.1

[56] References Cited

PUBLICATIONS

Chao et al. Nature, vol. 380, pp. 396–397, Apr. 4, 1996.
Ericksson et al, Journal of Virological Methods 59: 127–133, May 1996.

*Primary Examiner*—Mary E. Mosher
*Attorney, Agent, or Firm*—Smith, Gambrell & Russell, LLP; Beveridge, DeGrandi, Weilacher & Young Intellectual Property Group

[57] ABSTRACT

Green fluorescent protein (GFP) gene was transplanted into baculovirus. The baculovirus was used to infect pests of vegetable crops. Three to five days after infection, the infected insects were found to emit strong fluorescence when exposed to a portable UV light. Therefore the spreading of baculovirus infection and disease progression can be effectively detected in the field. In addition, the GFP reduced UV damage to the baculovirus. As a result, GFP can increase the retention time of the virus as a pesticide in the field.

7 Claims, 2 Drawing Sheets

FIG. 2

USE OF GREEN FLUORESCENT PROTEIN TO TRACE THE INFECTION OF BACULOVIRUS IN INSECTS AND TO INCREASE VIRAL UV STABILITY

FIELD OF THE INVENTION

This invention is to transplant GFP gene into type baculovirus, the *Autographa californica* multiple nuclear polyhedrons virus (AcMNPV), and then to infect diamondback moths (DBM), beet army worms and cabbage loopers with AcMNPV bearing GFP. This method can be used to detect AcMNPV infection of pest insects in field. In addition, it can eliminate ultraviolet (UV) lights in sunlight and reduce the damage of sunshine sunlight to the virus for better viral infection to pest insects.

DESCRIPTION OF PRIOR ART

Conventionally, AcMNPV is a microscopic creature. It can not be seen and traced on vegetable crops. Therefore, entomologists had been using imprecise methods to evaluate the pesticidal effects. The evaluation methods include: calculating the amount of dead insects after virus spray and the time demand to fatality. The main disadvantage of this method is that the nearly and previously dead insects are subject to dropping then decomposing on the ground or being eaten by birds and animals. As the result, they could not be traced. Moreover, it is difficult for virologists to precisely determine the insects that are killed by the virus rather than other microorganisms on field vegetable crops or other ecological factors.

In addition, another method to evaluate the pesticidal effect is to measure the reduction of damaged leave area. This is an indirect method. Although it is not ineffective, to mark virus directly is much more precise. Therefore, the inventor marked GFP gene on AcMNPV and found that this is an excellent ecological tracing method.

SUMMARY OF THE INVENTION

The purpose of this invention is to provide a method to trace baculovirus infection fast and effectively on field insects.

Another purpose of this invention is to precisely determine the pesticidal effects of viruses, using AcMNPV as a model to achieve this goal.

BRIEF DESCRIPTION OF DRAWINGS

The file of this patent contains at least one drawing (photograph) executed in color. Copies of this patent with color drawings will be provided by the Patent and Trademark Office upon request and payment of the necessary fee.

In order that the present invention may more readily be understood, the following description is given, merely by way of example with reference to the accompanying drawings, in which:

FIG. 2 is a chart of experimental results of GFP protection on occlusion bodies of AcMNPV wherein moths infected with different AcMNPVs were exposed to UV for 5 hours (left three bars) versus no exposure (right three bars), the occlusion bodies of AcMNPVs were then purified and fed to the third-stage beet army worms, the pesticidal efficiencies of different AcMNPVs were calculated, Ac-GFP is AcMNPV containing GFP gene, AcMNPV is wild AcMNPV and AclacZ is AcMNPV containing lacZ gene, the virus containing lacZ gene does not glow under UV exposure, therefore, it can be used as another control virus besides wild AcMNPV.

DETAILED DESCRIPTION OF EMBODIMENT

The green fluorescent protein (GFP) is from a jelly fish, *Aeguorea Victoria*. The jelly fish produces the GFP that can be excited by the blue lights or long-wave-length UV lights that are remains of sun penetration through the sea water. Green fluorescence is then emitted upon excitation. We obtained this gene from commercial sources and transplant the gene into *Autographa california* multiple nuclear polyhedrons virus (AcMNPV). This refers to the O'Reilly et al's Baculovirus Expression Vectors (Freeman, Oxford, 1992). The GFP is a very stable protein. It can emit green lights under the excitement of 395 nm or 470 nm lights.

A complete nucleic acid sequence is derived from plasmid pGFP (Kein S. R. et al., 1995, *Biotechniques* 19, 650–855) and inserted into vector pAcUW21(PharMingen Inc., USA). Under the control of strong P10 promoter of baculovirus, AcMNPV. A large amount of GFP protein can be produced in cells or insects by this promoter.

This vector combining with AcMNPV DNA were then co-transfected into Spodoptera frugiperda (Sf21) cells. After a week, viruses in the medium were collected and diluted through time dilution series. The diluted viruses are analyzed and purified by plaque assay. When a using fluorescent microscope with a 488 nm fluorescent filter, a strong green fluorescence can be observed two days after the infection. It is more clear four days after infection. Therefore, cells containing recombinant viruses can be easily separated. The cells emitting fluorescence can be easily detected and used for further purification of recombinant viruses. This method does not need complicated probe cross detection or polymerase chain reaction analysis.

Figure 1A:
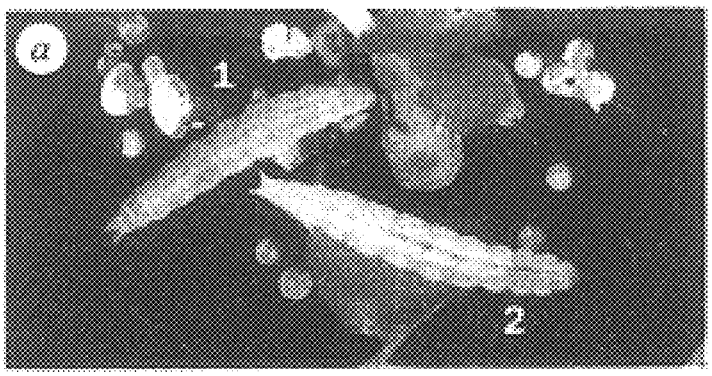
FIG. 1 are photos showing AcMNPV bearing GFP gene causing the infected DBMs emitting fluorescence, A: Photo of a non-infected DBM (a) and an infected DBM (b) under visual lights, B-D: Photo of the indicated DBMs under UV lights and the photos of B-D show that worm (b) is on the move.
Figure 1B:
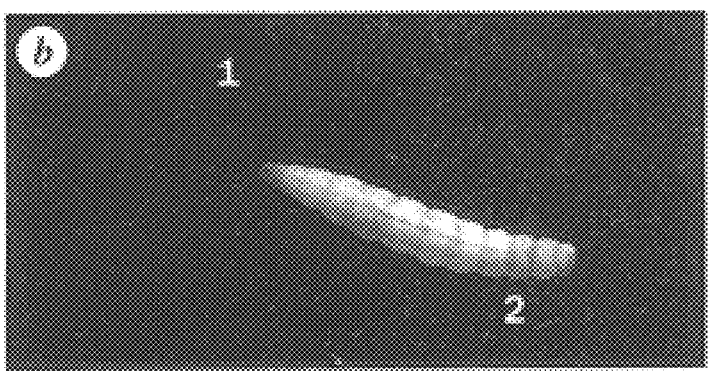
Figure 1C:
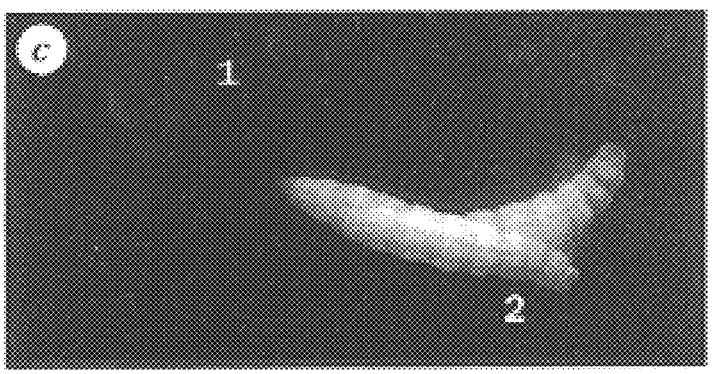
Figure 1D:
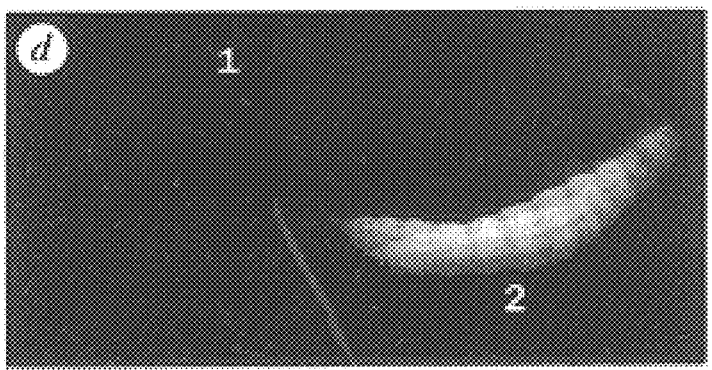

After the larvae were infected with this genetically engineered virus, strong, continuous and whole-body fluorescence were emitted. Due to the use of a strong viral promoter and viral replication the fluorescence is enhanced extensively. Moreover, the virus can infect most cells in insects, which makes essentially the entire worm body emit glorious lights, referring to FIG. 1. These highly intensive and wholly somatic lights can not be achieved by inserting GFP gene directly into the genonre of insect cells.

Conventionally, lacZ is used as a marker gene for the screening of recombinant virus,. This method has been applied to Vaccinis Virus (Chakrebarti S. et al., 1985, *MOI. Cell Biol.* 5, 3403–3409) and AcMNPV (Vialard J et al., 1990, *J Virol.*, 64, 37–50).

The experimental results of the inventor indicate that GFP gene can be a substitution of lacZ gene. Therefore, the expensive substrate and toxic solvents can be avoided. Yet, we can successfully detect the existence of recombinant AcMNPV in the living infected cells. Moreover, this invention provides a convenient and harmless method to detect target cells and viruses. It also avoids the contamination of culture solution when introducing the substrate.

This invention is to transplant GFP gene into type baculovirus, the *Autographa California* Multiple Nuclear Polyhedrons Virus (AcMNPV) and then to infect important pests of main vegetable crops. The tested materials are:

diamondback moth, beet army worm and cabbage looper. Three to five days after infection, when exposed to 365 nm UV light, the infected insects were found to emit strong fluorescent lights. On the contrary, uninfected insects emit no fluorescent lights. Therefore, this invention can be used to effectively detect the spreading and disease progressing of AcMNPV infection in insects field. In addition, we found that GFP could convert UV lights in sunlight into harmless green lights, and reduce the damage of the virus. As a result, GFP can increase the retention time of the virus in field so that the virus can kill pests constantly and effectively.

The green fluorescence emitted by virus-infected cells can also be detected and classified using a FACS machine. This is also true even when the concentration of recombinant virus is low (m. o. i.=0.1). Using a FACS machine, we can easily separate the fluorescence-emission cells and non-fluorescence-emission cells and analyze the activities of promoters. Unfortunately, although the expressivities of lacZ gene in mammal cells (Fiering, S. N. et al., 1991, *Cytometry* 12, 291–301) and in AcMNPV can all be detected by FACS machine, this method requires the addition of substrates. This leads to high costs and troubles. It is also subject to contamination of cells. On the contrary, using GFP as a reporter does not have these annoyances. Consequently, utilization of GFP provides a more reliable and precise method to analyze promoters.

AcMNPV broadly infests Lepidopteran insects, including diamondback moth (DBM) and *Plutelia xylostella* L. (Lepidoptera). Therefore, DBM can be used to specify the practicability of the new GFP-detection system. DBM is the most destructive insect and distributed widely in the whole world (Talekar N. S. and Shelton A. M., 1993, *Annu. Rev. Entomol.*, 38, 275–301). It is reported in many countries that DBM has developed a high pesticide resistance. Some researchers have been studying biological control methods, including, improving AcMNPV by genetic engineering (Talekar N. S. and Shelton A. M) (practical cases).

The occlusion body of AcMNPV containing GFP gene is fed to the third-stage primary larvae of DBM. At 26° C., 3–5 days after infection, we can observe the emission of fluorescence by holding a long-wave-length (365 nm) UV lamp (FIG. 1.). At 26° C., the fluorescence can be detected on infected insects four days before their deaths. Under constant UV exposure, the fluorescence would last for at least 5 hours or sustain over 10 hours under intermittent exposure. Yet the intensity of fluorescent emissions would not apparently diminish. The infected worm body can radiate for a certain long time. At 22° C., the fluorescence would last for at least 4 days. Whereas at 4° C., it would remain strong for 10 days. This is also true even though the larvae have been killed for 6 days. The fluorescent emission is strong. It can be used to identify the infected individuals among numerous healthy larvae. In further developments, this method will provide a brand-new and useful tool to evaluate the infected larvae precisely and conveniently on field crops. Using this tool, researchers would be able to avoid the situation that they only collect seriously infected insects and ignore the insects that are symptomless but still developing the disease. The seriously infected larvae usually drop dead and disappear within a short time. Therefore, they are difficult to enumerate. Utilization of GFP recombinant viruses does not need troublesome molecular analyses to determine whether the deaths of insects are caused by the released viruses or other pathogens in the environment.

For improving AcMNPV as a pesticidal pathogen, some experimental researchers have inserted an insect-specific toxic, or hormone genes, into the genome of AcMNPV (Tomalski and Miller,1991, *Nature* 352, 82–85). Before the extended usage of these viruses, the recombinant AcMNPV containing GFP gene of the same design can be used to predict the width and depth of their distribution and estimate their impacts to the environment. Since this method only requires a portable long-wave-length UV source to detect the infected larvae, it has a sufficient applicability.

Figure 2:
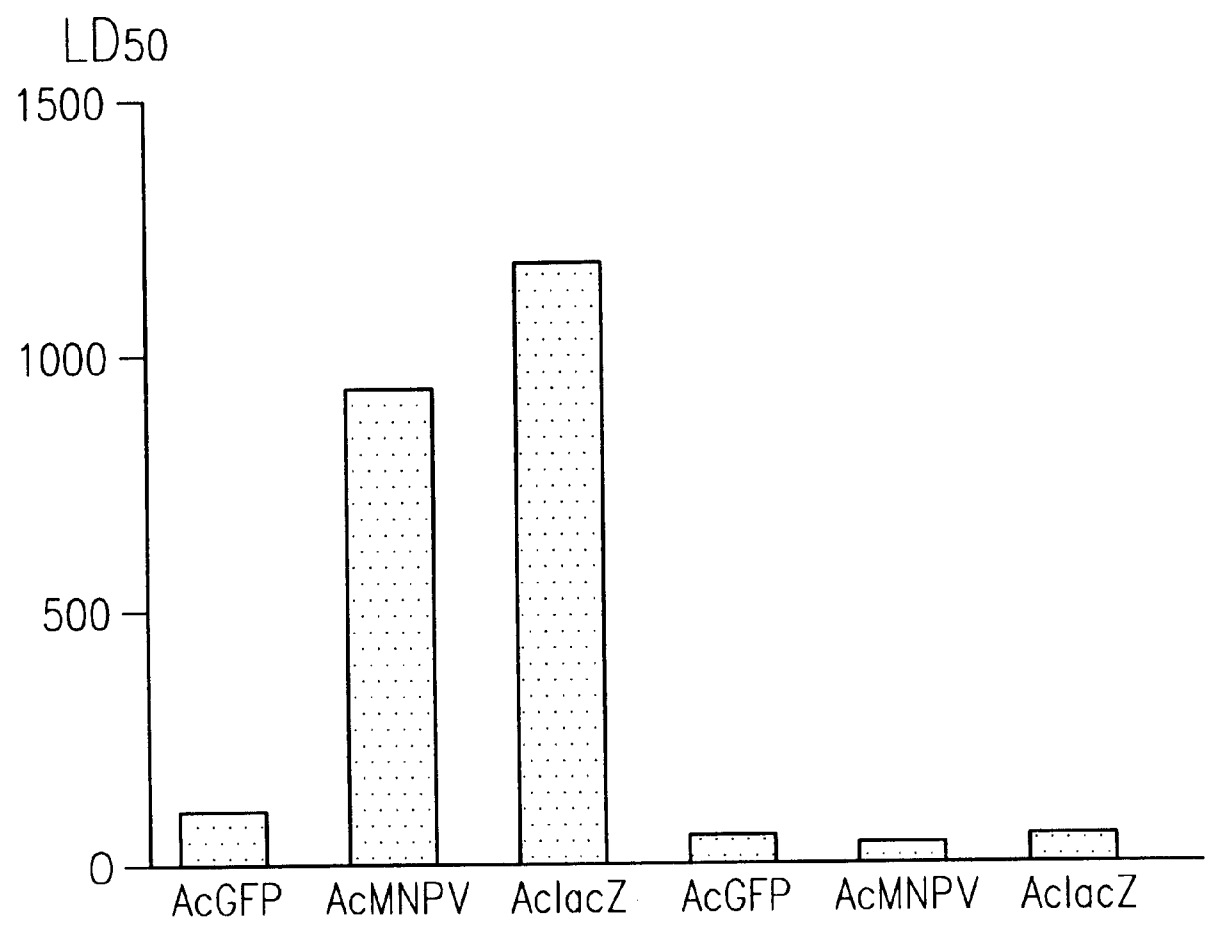

In addition, because GFP can convert hazardous UV lights into harmless green lights, the experimental results show it is capable to protect AcMNPV. In the 5-hour long-wave-length UV exposure, the pesticidal efficiency of AcMNPV did not change too much. On the contrary, without the protection of GFP, the pesticidal efficiency would reduce by up to 20 times, referring to FIG. 2. Therefore, this is a great benefit on the field application in the future.

I claim:

1. A method of pesticidal treatment with enhanced UV stability comprising:

administering a baculovirus containing a green fluorescent gene protein to insects on crop plants under conditions where the insects are exposed to UV radiation.

2. The method of claim 1 wherein the baculovirus is an *autographa californica* multiple nuclear polyhedrosis virus.

3. The method of claim 2 wherein the ultraviolet radiation is solar ultraviolet radiation.

4. The method of claim 3 wherein the *autographa californica* multiple nuclear polyhedrosis virus is administered in spray.

5. The method of claim 2 wherein the *autographa californica* multiple nuclear polyhedrosis virus is obtained from the body of an insect or an insect larvae.

6. The method of claim 5 wherein the insect or insect larvae is selected from the group consisting of a diamondback moth, a beet army worm and a cabbage looper.

7. A method of improving the UV stability of a pesticidal baculovirus, comprising:

inserting a green fluorescent protein gene in the baculovirus; and administering the baculovirus to an insect on a crop plant under conditions where the insect is exposed to UV radiation.

* * * * *